United States Patent
Eickhoff et al.

(10) Patent No.: US 6,693,283 B2
(45) Date of Patent: Feb. 17, 2004

(54) BEAM SCANNING SYSTEM FOR A HEAVY ION GANTRY

(75) Inventors: Hartmut Eickhoff, Darmstadt (DE); Thomas Haberer, Darmstadt (DE); Peter Spiller, Darmstadt (DE); Marius Pavlovic, Darmstadt (DE)

(73) Assignee: Gesellschaft fuer Schwerionenforschung mbH, Darmstadt (DE)

( * ) Notice: Subject to any disclaimer, the term of this patent is extended or adjusted under 35 U.S.C. 154(b) by 0 days.

(21) Appl. No.: 10/240,518

(22) PCT Filed: Feb. 6, 2002

(86) PCT No.: PCT/EP02/01237
§ 371 (c)(1),
(2), (4) Date: Apr. 16, 2003

(87) PCT Pub. No.: WO02/069350
PCT Pub. Date: Sep. 6, 2002

(65) Prior Publication Data
US 2003/0164458 A1 Sep. 4, 2003

(30) Foreign Application Priority Data

Feb. 6, 2001 (EP) .............................. 01102708
Feb. 6, 2001 (EP) .............................. 01102709
Feb. 6, 2001 (EP) .............................. 01102710

(51) Int. Cl.[7] .......................... H01J 37/147; G21K 5/10
(52) U.S. Cl. .............................. 250/396 ML; 250/398; 250/492.3
(58) Field of Search .................... 250/492.3, 398, 250/396 ML (56) References Cited

U.S. PATENT DOCUMENTS

| | | | |
|---|---|---|---|
| 4,870,287 A | * | 9/1989 | Cole et al. ............... 250/492.3 |
| 5,393,984 A | * | 2/1995 | Glavish ............... 250/396 ML |
| 6,476,403 B1 | * | 11/2002 | Dolinskii et al. ........ 250/492.3 |

OTHER PUBLICATIONS

Milburn et al.: "Raster scanning magnets for relativistic heavy ions" *Proceedings of the 1987 IEEE Particle Accelerator Conference: Accelerator Engineering and Technology* (Cat. No. 87CH2387-9) Washington, D.C., USA Mar. 16–19, 1987, pp. 2000–2002.
Haberer et al.: "Magnetic Scanning System for Heavy Ion Therapy", *Nuclear Instruments & Methods in Physics Research, Section—A: Accerlerators, Spectrometers, Detectors and Associated Equipment*, North–Holland Publishing Company, Amsterdam NL, vol. A330 No. 1/2, Jun. 10, 1993, pp. 296–305.

* cited by examiner

Primary Examiner—Jack Berman
(74) Attorney, Agent, or Firm—Frommer Lawrence & Haug, LLP; Ronald R. Santucci (57) ABSTRACT

The present invention relates to a scanning System for a heavy ion gantry comprising a scanner magnet (1–2; 3–4) for a high energy ion beam used in a heavy ion cancer therapy facility having a maximal bending angle ($\alpha$) of about 1.5. degree; a curvature radius of about 22 m; a path length of about 0.6 m and a gap height (h) and a gap width (w) in the range of 120 mm to 150 mm. Further each scanner magnet (1–2, 3–4) comprises one glued yoke element made of steel plates having a thickness of up to 0.3 mm and being alloyed with up to 2% silicon. This yoke element has a width in the range of 300 mm to 400 mm, a height in the range of 200 mm to 250 mm and a length in the range of 500 to 600 mm. A coil for each scanner magnet (1–2; 3–4) has a number of windings in the range of 50 to 70. Further the system (11) comprises a 90 degree dipole (6) positioned downstream of said scanner magnets (1–2; 3–4) having an aperture adapted to the scanning area, and enclosing a yoke element with gaps to increase the homogeneity of the electric field. Additionally the system encloses beam diagnostic plate type detectors (7) stapled downstream of said 90 degree bending magnet (6).

9 Claims, 8 Drawing Sheets

Fig. 1: Schematic drawing of the Scanning system.

Beam angle as a function of the exit edge angle

Fig. 4

Scanner angles as a function of the exit edge angle

Fig. 5

Transverse distribution of the integral flux density at two longitudinal positions and field levels.

Fig. 6

Steady state fringing field decay of the 90 degree gantry dipole magnet along the optical axis. Indicated is the position of the edge of the yoke and the position of the screening plate.

Fig. 7

After ramping, the static magnetic field in the 90 degree dipole magnet is effected by transient processes. Eddy currents in the yoke generate a time dependend magnetic fields which deforms the main and stray field field.

Fig. 8

Calculated beam intensity distributions at different positions in the scan field.
The overall dimensions of each frame are 5 x 5 mm.

Fig. 9

Characteristic particle tracks through the gantry system. Shown is an example for beam scanning to the outermost positions in the ISO plane.

BEAM SCANNING SYSTEM FOR A HEAVY ION GANTRY

This application is a 371 of PCT/EP02/01237 filed on Feb. 6, 2002, and claims priority benefits of European applications, EP 01 102 710.9 filed Feb. 6, 2001, EP 01 102 709.1 filed Feb. 6, 2001 and EP 01 102 708.3 filed Feb. 6, 2001.

The present invention relates to a scanning System for a heavy ion gantry used in a heavy ion cancer therapy facility according to the subject matter of claim 1.

From U.S. Pat. No. 4,870,287 a proton beam therapy system is known for selectively generating and transporting proton beams from a single proton source and accelerator to selected ones of a plurality of patient treatment stations each having a rotatable gantry for delivering the proton beam at different angles to patients supported in fixed orientations at the stations.

Further it is known from U.S. Pat. No. 4,870,287 a new imaging technique like a computed tomography scanning which uses a scanning technique to identify the exact location of the site to be treated, but there is no hint in U.S. Pat. No. 4,870,287 for applying a scanning magnet to directly and precisely move or bend the therapy beam to the exact location of the site to be treated.

From H. Eickhoff et al. "The proposed accelerator facility for light ion cancer therapy in Heidelberg" (Proc. Of the IEEE Part. Acc. Conf. NY, 1999, p 2513–2515) an intensity-controlled raster scan technique is known to move or bend the ion beam of a therapy system. However, neither the scanning magnets are defined nor the position of these scanning magnets within the therapy system are disclosed.

Thus, it is an object of the present invention to define and provide a scanner magnet for a high energy ion beam used in a heavy ion cancer therapy facility. It is particularly an object of the present invention to provide a combination of a scanner magnet positioned upstream a last bending magnet.

This object is achieved by the subject matter of independent claim 1. Features of preferred embodiments are disclosed by dependent claims.

According to the present invention a scanning System for a heavy ion gantry is provided comprising a scanner magnet for a high energy ion beam used in a heavy ion cancer therapy facility having a maximal bending angle ($\alpha$) of about 1.5 degree; a curvature radius of about 22 m; a path length of about 0.6 m and a gap height (h) and a gap width (w) in the range of 120 mm to 150 mm. Further each scanner magnet (1–2, 3–4) comprises one glued yoke element made of steel plates having a thickness of up to 0.3 mm and being alloyed with up to 2% silicon. This yoke element has a width in the range of 300 mm to 400 mm, a height in the range of 200 mm to 250 mm and a length in the range of 500 to 600 mm. A coil for each scanner magnet has a number of windings in the range of 50 to 70. Further the system comprises a 90 degree Dipole positioned downstream of said scanner magnets having an aperture adapted to the scanning area, and enclosing a yoke element with gaps to increase the homogeneity of the electric field. Additionally the system encloses beam diagnostic plate type detectors stapled downstream of said 90 degree bending magnet.

Such a scanning system has the advantage that it controls the direction of an ion beam at the location of the ISO-plane or ISO-center over a scan field of 200×200 mm, when at least two scanning magnets are applied as horizontal and vertical dipole magnets.

In a preferred embodiment said scanning magnets are positioned within a gantry system of a heavy ion cancer therapy system upstream of the last 90 degree bending magnet. This position has the advantage that the space for the patient treatment position is not decreased or limited by the volume of the scanning magnets. The overall radius of the Gantry is minimized and the Gantry weight is decreased. Said scanning magnets in combination with said a 90 degree bending dipole having an appropriate yoke with defined gaps and an appropriate exit edge angle a parallel scanning downstream said 90 degree bending dipole is possible.

Preferably the coil of said scanner magnet is designed to tolerate a maximum coil current in the range of 500 to 600 A. Such a high coil current is supplied to said 50 to 70 turns of said coil, to perform a maximum bending angle of the ion beam of about 1.5 degree.

To manage the heat loss of such a coil the scanner magnet is water-cooled by plurality of cooling channels preferably by at least six cooling channels and preferably by a total cooling water supply in the range of 5 l/min to 10 l/min. Such a water cooled coil has the advantage to increase the safety of operation during patient treatment compared to Hydrogen or Nitrogen cooled super conductive coils.

In a further preferred embodiment the coil is not superconductive but has a coil resistance in the range of 30 m$\Omega$ and 50 m$\Omega$ which causes a maximum DC-power consumption in the range of 10 KW to 12 KW.

To guarantee said maximum bending angle the total coil inductance of said scanner magnet is in the range of 3 to 4 mH.

The total supply voltage for the coil is preferably in the range of ±350 V to ±400 V to maintain the maximum coil current in each bending direction.

In a further preferred embodiment said scanner magnet comprises one single yoke-segment. This has the advantage of a simple construction and an easy maintenance and assembly-handling of the scanner system which minimizes the operational costs.

The 90 degree dipole provides a homogeneity of the electric field of about $+-2\times10^{-4}$. Such a homogeneity of the electric field avoids image errors and elliptic beam spots. The gaps within the yoke of the bending dipole has the advantage, that the homogeneity of such a large scanning area of 23×23 cm is in the above mentioned limits at the ISO center of the gantry.

Since there might occur saturation effects at the exit of the 90 degree bending Dipole having such edge angles, the Yoke cross section is locally increased. Further the maximum electric field is limited to 1.8 Tesla to minimize the saturation effects.

The overall weight of the bending dipole is about 72 t. The Yoke is divided into 6 segments each having four adjustment means.

The invention is now described in details with respect to the attached drawings.

Figure 10:
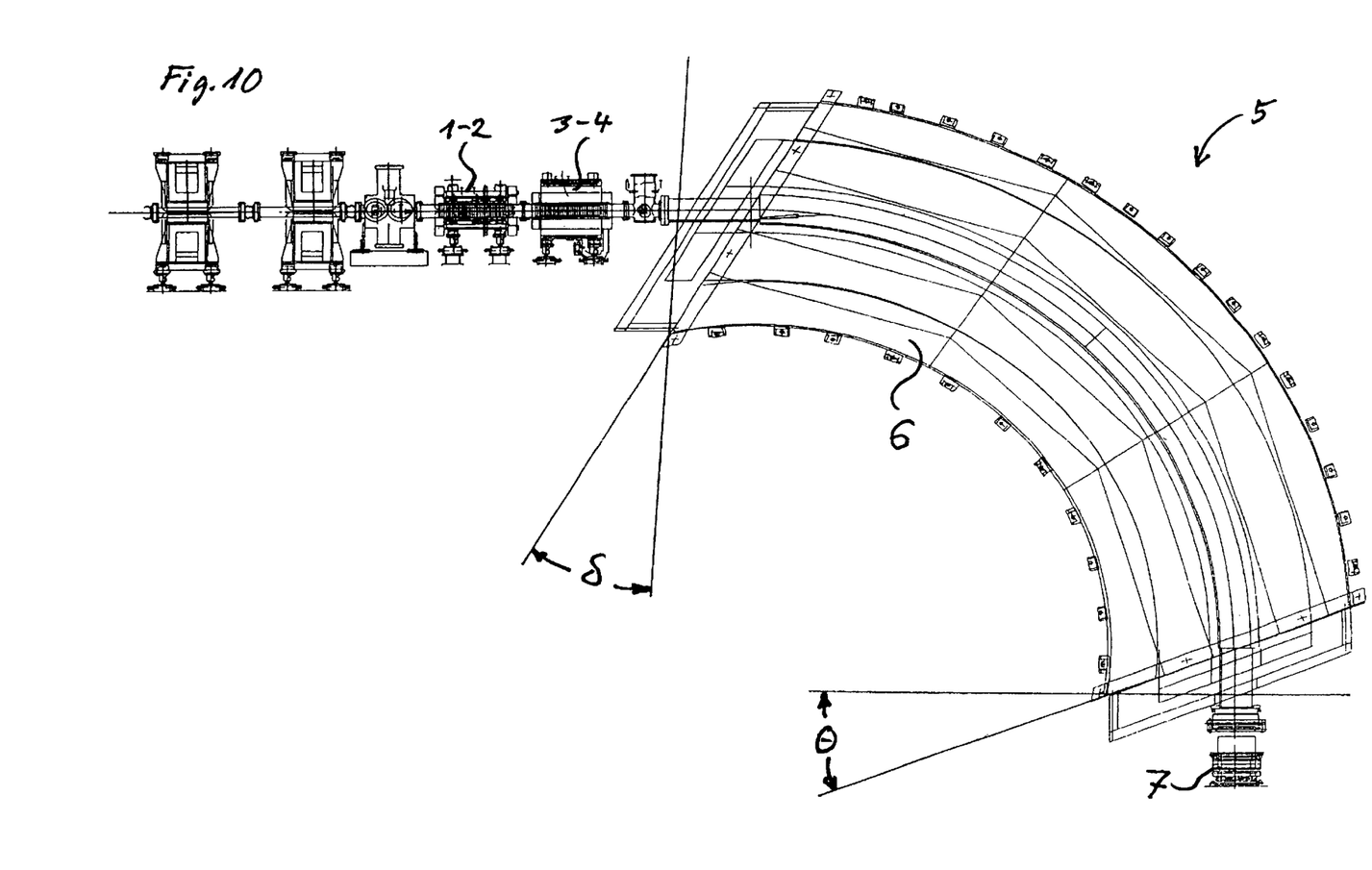
FIG. 10 shows a scanning system according to an embodiment of the present invention.

The beam scanning system 5, shown in FIG. 10, consisting of a rectangular, horizontal and a vertical dipole magnet 1–2 and 3–4, is located in front of the 90 degree dipole magnet 6. The aperture (23×23 cm) of the 90 degree dipole magnet 6 and the beam scanning system is designed for a scan field of 20×20 cm on the ISO plane. The exit edge angle θ of the 90 degree dipole magnet 6 strongly determines the final beam angle. At an exit edge angle θ of 21 degree the beam angles in both transverse planes are small (≈2.5 mrad) and equal in both transverse planes.

TABLE 1

| type | | Dipole (WF-type) |
|---|---|---|
| bending angle | [°] | 1.45 |
| curvature-radius | [m] | 21.6 |
| pathlength | [m] | 0.547 |
| yoke length | [m] | 0.44 |
| yoke height | [m] | 0.23 |
| yoke width | [m] | 0.35 |
| thickness of laminates | [mm] | 0.3 |
| maximum flux density | [T] | 0.31 |
| field homogeneity $\delta = \Delta B/B$ | | $\pm 5 * 10^{-4}$ |
| edge-angle | [°] | 0° ? |
| number of yoke-segments | | 1 |
| area of field-hom. δ (height, width) | [mm$^2$] | 120 * 120 |
| geom. gap height | [mm] | 130 |
| geom. gap width | [mm] | 140 |
| total number of windings | | 60 |
| maximum coil current $I_{max}$ | [A] | 535 |
| current accuracy $\delta I/I_{max}$ | | $<1 * 10^{-4}$ |
| max. DC-voltage | [V] | 19.4 |
| total coil resistance | [mΩ] | 36.2 |

TABLE 1-continued

| type | | Dipole (WF-type) |
|---|---|---|
| inductance | [mH] | 3.33 |
| maximum DC-power consumption | [kW] | 10.3 |
| ramping rate | [T/s] | 62 |
| maximum total voltage | [V] | +375 |
| number of cooling channels | | 6 |
| total cooling water supply | [l/min] | 7.5 |
| total weight | [to] | 0.22 |

Tab. 1. Parameters of the Scanner Magnets (for Hor., and Vert. Deflection)

Figure 1:
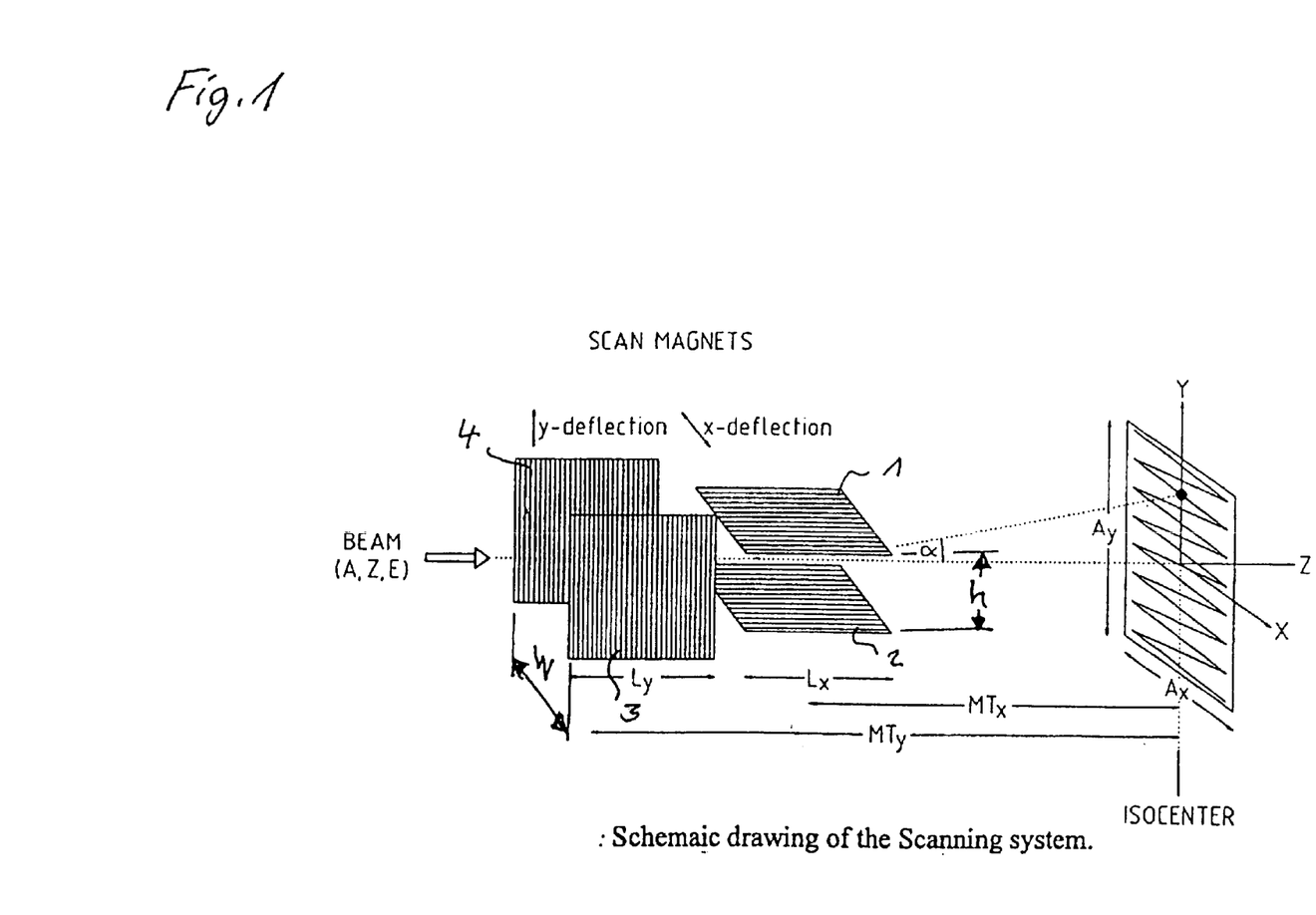
FIG. 1 shows a schematic drawing of the scanning system.

The beamlines for the treatment areas are equipped with nearly identical beam scanning systems shown in FIG. 1. These beam scanners consist out of a set of two fast orthogonally oriented dipole magnets located some meters upstream to the patient position. The differences arise from the fact that in the case of the gantries the drift space (≈7 m) downstream the last scanner dipole magnet is replaced or filled by a large aperture 90 degree bending magnet.

The steerer angles required to reach a certain transverse position in the ISO plane can be determined from ion optical calculations. Due to the effect of the edge angles of the dipole a calculated displacement do not agree precisely with simple trigonometrical estimation. The calculated scanner angles required to move the beam to some characteristic positions are listed in the following table 2. In addition to the effect of the edge angle the effect of the extended fringing field has an impact on the beam position and the beam shape in the ISO plane. The influence of the fringing field was investigated in third order by means of a computer code.

The left columns of the table show the scanner angles obtained by a first order approximation. The medium columns contain the results of the higher order calculations. It can be seen that the higher order aberrations cause a difference in beam position of up to 2 mm from the linear model. The right columns contain the difference measured in scanner angles required to compensate the aberration effects. In addition to the displacement, the higher order image aberration may cause the beam to get elliptical in the corners of the scan field. This effect depends strongly on the amplitude of the envelope in the fringing fields. For the magnet setting used as a reference gantry optics one goal was to minimize the envelope size in the dipole stray field.

TABLE 2

| Position (x, y) [mm] | Hor. Scanner angle [mrad] | Vert. Scanner Angle [mrad] | Hor. Shift Caused by Aberations [mm] | Vert. shift Caused by Aberations [mm] | Hor. Scanner Correction [mrad] | Vert. Scanner Correction [mrad] |
|---|---|---|---|---|---|---|
| −10/+10 | 21.73 | −15.67 | −2.1 | 1.1 | −0.46 | 0.14 |
| 0/+10 | 0 | −15.65 | −1.9 | 0 | −0.0004 | 0 |
| +10/+10 | −21.73 | −15.67 | −2.0 | −0.9 | −0.46 | −0.16 |
| −10/0 | 21.73 | 0 | −0.2 | 0 | 0 | 0 |
| 0/0 | 0 | 0 | 0 | 0 | 0 | 0 |
| +10/0 | −21.74 | 0 | −0.1 | 0 | 0 | 0 |
| −10/−10 | 21.73 | 15.65 | −2.0 | −0.8 | −0.46 | −0.12 |
| 0/−10 | 0 | 15.7 | −1.8 | −0.1 | −0.0004 | 0 |
| +10/−10 | −21.73 | 15.65 | −2.1 | 1.2 | −0.46 | 0.19 |

FIG. 1 shows a schematic view of the scanner geometry. The scanned beams will cover 20×20 cm$^2$, this corresponds to deflection angles of ≈±0.85 degrees. The geometrical precision is expected to be in the order of ±0.25 mm, whereas the typical stepsize from beamposition to beamposition will be 1–5 mm.

Assuming a drift without active optical elements, the displacement of the beam in the horizontal (x) and vertical (y) direction in the ISO-plane can be estimated according to:

$$x = z_1 \tan(a_x) \text{ and } y = z_2 \tan g(a_y)$$

with $z_1$ being the distance of the horizontal scanner from the ISO plane ($z_1$=8.955 m) and $z_2$ being the distance of the vertical scanner from the ISO plane ($Z_2$=9.805 m) and $a_x$ and $a_y$ the corresponding scanner angles. The scanner magnets as specified, bend a beam with maximum magnetic rigidity of 6.6 Tm, 1.5° at a coil current of 540 A. Thus the equations can be written as:

$$x = 8.955 \, m \tan(1.5°/540 A \cdot I_x) \text{ and } y = 9.805 \, m \tan(1.5°/540 A \cdot I_y)$$

with $I_{x/y}$ being the momentary scanner current. For the calculation of the acceptable coil current tolerances a maximum x,y displacement of 0.1 mm is assumed. The corresponding current can be calculated to be $I_y$=210 mA and $I_x$=230 mA.

The dipole edge angles cause a vertical focusing and a horizontal defocusing of the ion beam. Furthermore the effect of the fringing field may be considered. The fringing fields lead to a slightly nonlinear dependence of the beam position in the ISO plane from the scanner angles. This effect is rather small and can be neglected here. The effect of the edge angles, especially those of the exit, lead to a reduced displacement of the beam in the ISO plane at a certain scanner angle. E.g. the maximum displacements of x=0.1 m and y=0.1 m in the ISO plane is reached at scanner angles $a_y$=15.515 mrad=0.889° and $a_x$=21.27 mad=1.219°. According to the pure drift approximation, these angles would be: $a_y$=10.19 mrad=0.584° and $a_x$=11.17 mrad=0.64°. Thus the acceptable deviation from the nominal current at maximum displacement is relaxed by a factor of 1.52 for the vertical and by a factor of 1.9 for the horizontal plane.

Figure 2:
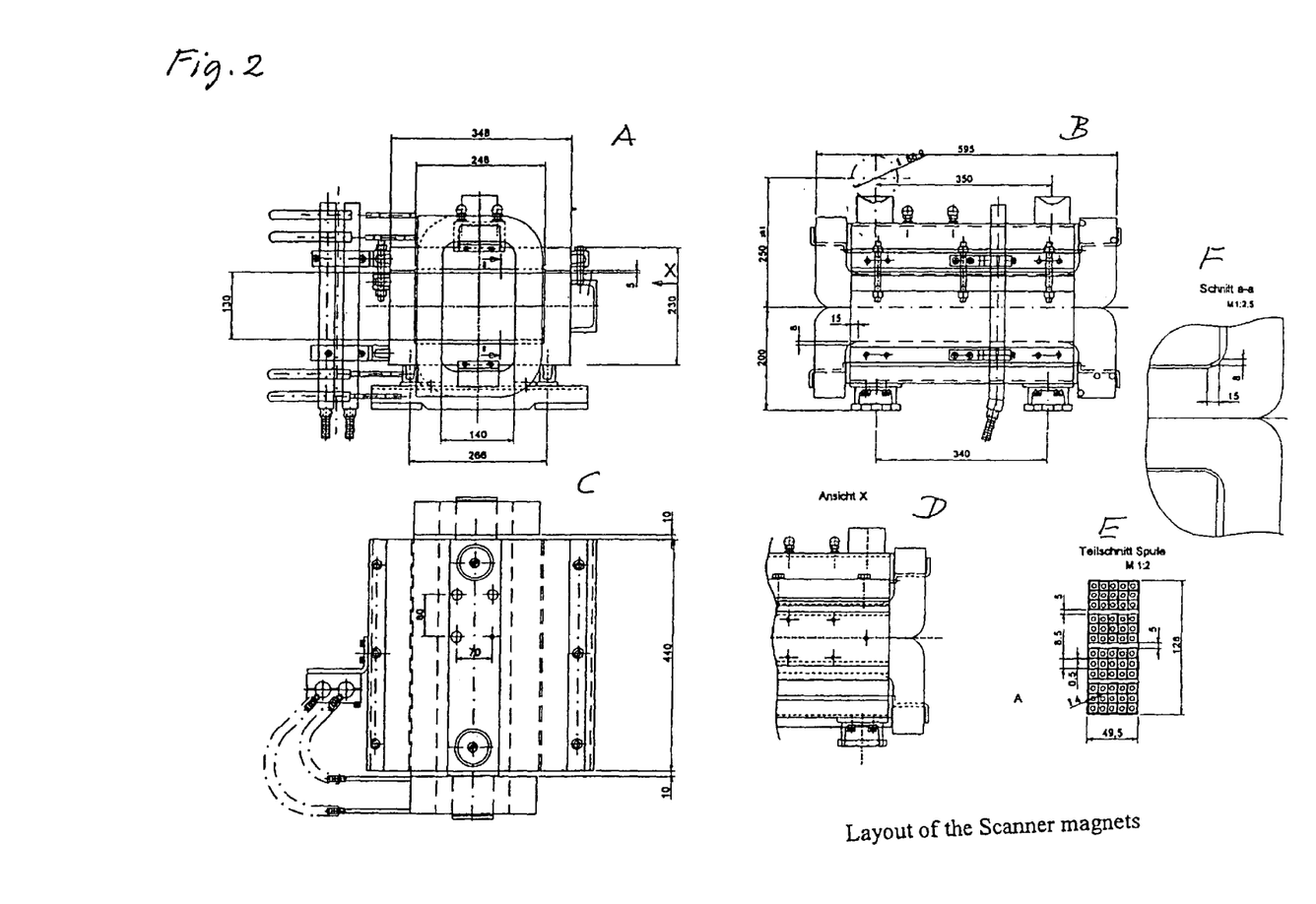
FIGS. 2 show different views of the layout of scanner magnets.

FIGS. 2A to 2C are self explaining and show different views of the layout of scanner magnets 1–2 and 3–4. FIG. 2D shows a view in X– direction of FIG. 2A. FIG. 2E shows a cross sectional view of the coil of a scanner magnet.

Figure 3:
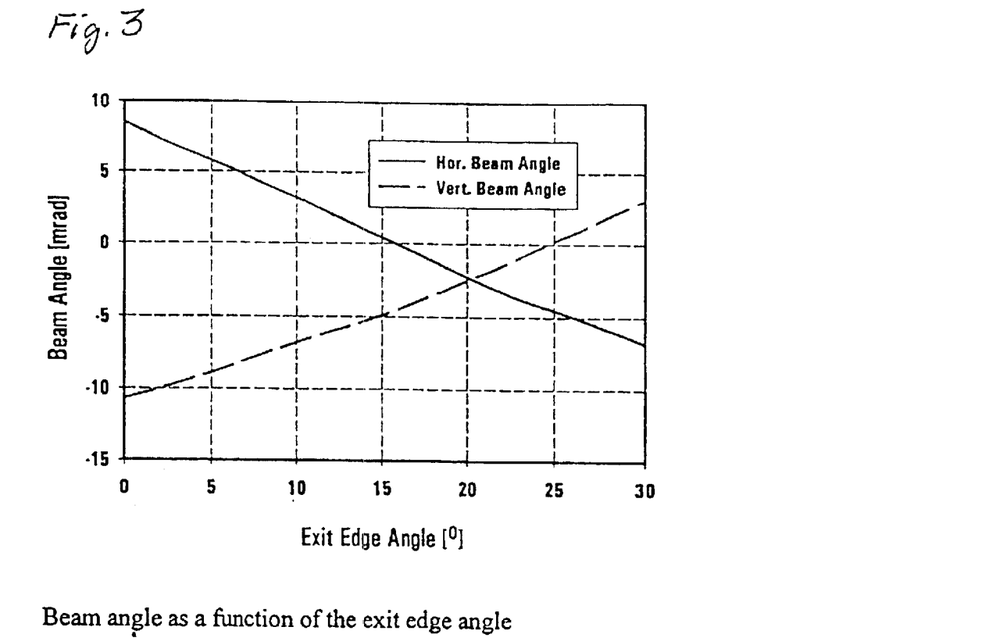
FIG. 3 shows beam angles as a function of the exit edge angle.

FIG. 3 shows beam angles as a function of the exit edge angle. The edge angle is chosen so that the beam has the smallest angle possible in respect to the optical axis to provide approximately a parallel scanning. The figure shows that the beam angle is approximately equal and small (parallel scanning) at an exit edge angle of 21 degree for the 90 degree bending magnet in combination with the scanning system.

Figure 4:
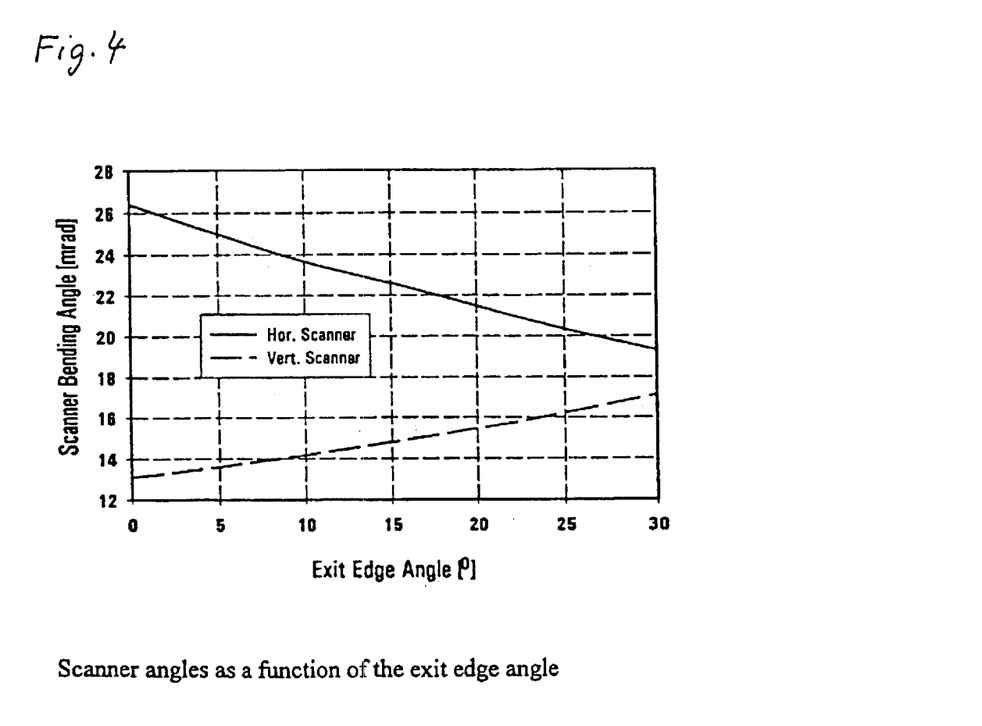
FIG. 4 shows scanner angles as a function of the exit edge angle.

FIG. 4 shows maximal scanner angles as a function of different exit edge angles. The maximal scanner angle depends strongly on the edge focusing or defocusing.

Figure 5:
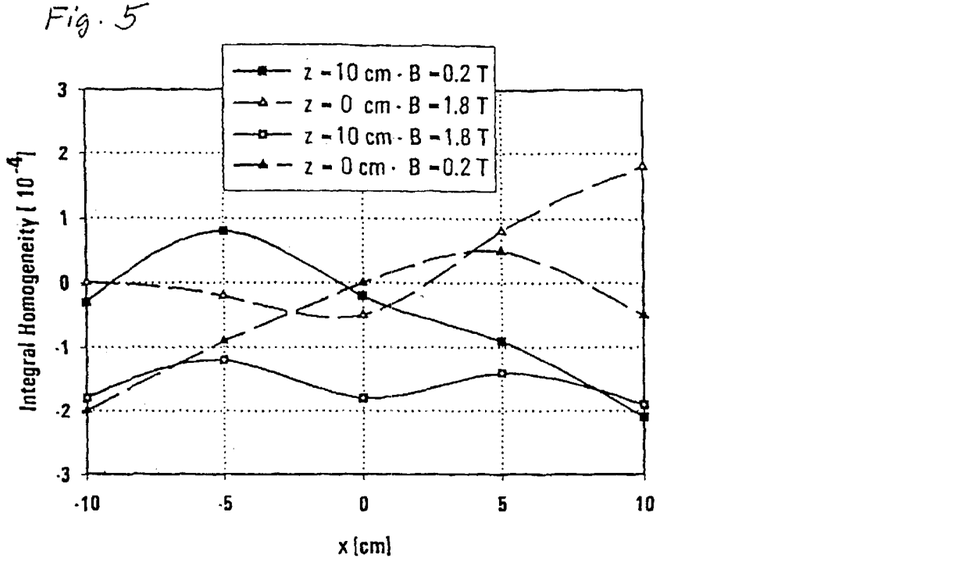
FIG. 5 shows a traverse distribution of the integral flux density.

FIG. 5 shows a traverse distribution of the integral flux density. The curves are calculated for the transversal flux density at two positions and two electric field densities.

Figure 6:
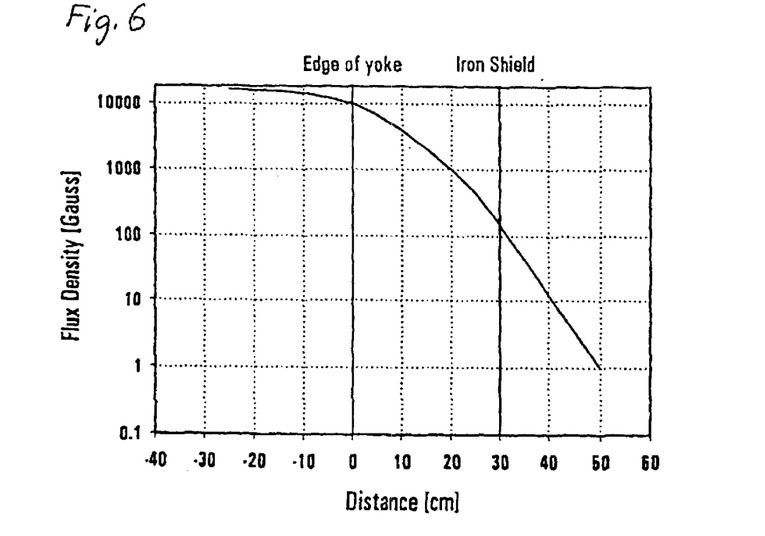
FIG. 6 shows a steady state fringing field decay, indicating the position of the edge of the one yoke of the scanner magnet.

FIG. 6 shows a steady state fringing field decay of the 90 degree gantry dipole magnet along the optical axis. Indicated is the position of the edge of the yoke and the position of a screening plate. It shows that the field is decreasing rapidly and falls below the legally allowed limit in the range of the patient.

Figure 7:
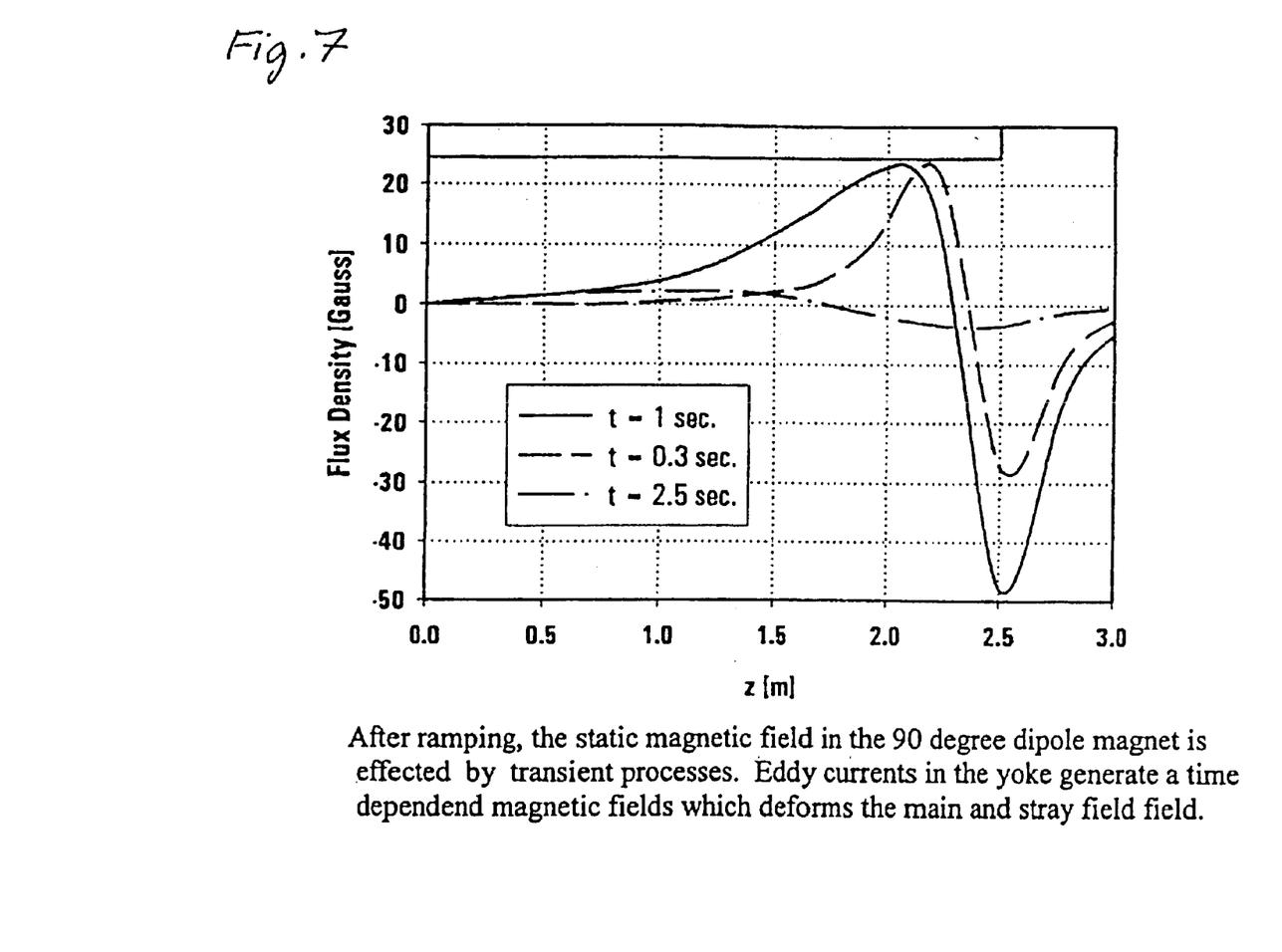
FIG. 7 shows flux density variations generated by Eddy currents in the yoke.

FIG. 7 shows flux density variations. Particularly it shows the effect of eddy currents within the yoke after the current ramp. After ramping the statistic magnetic field in the 90 degree dipole magnet is effected by transient processes. Eddy currents in the yoke generate time dependent magnetic field which deforms the main and stray field. The Eddy currents provide a local decrease up to three seconds. Therefore one has to wait until the beam therapy may start. The Eddy currents increase with the ramp velocity and with increasing flux density.

Figure 8:
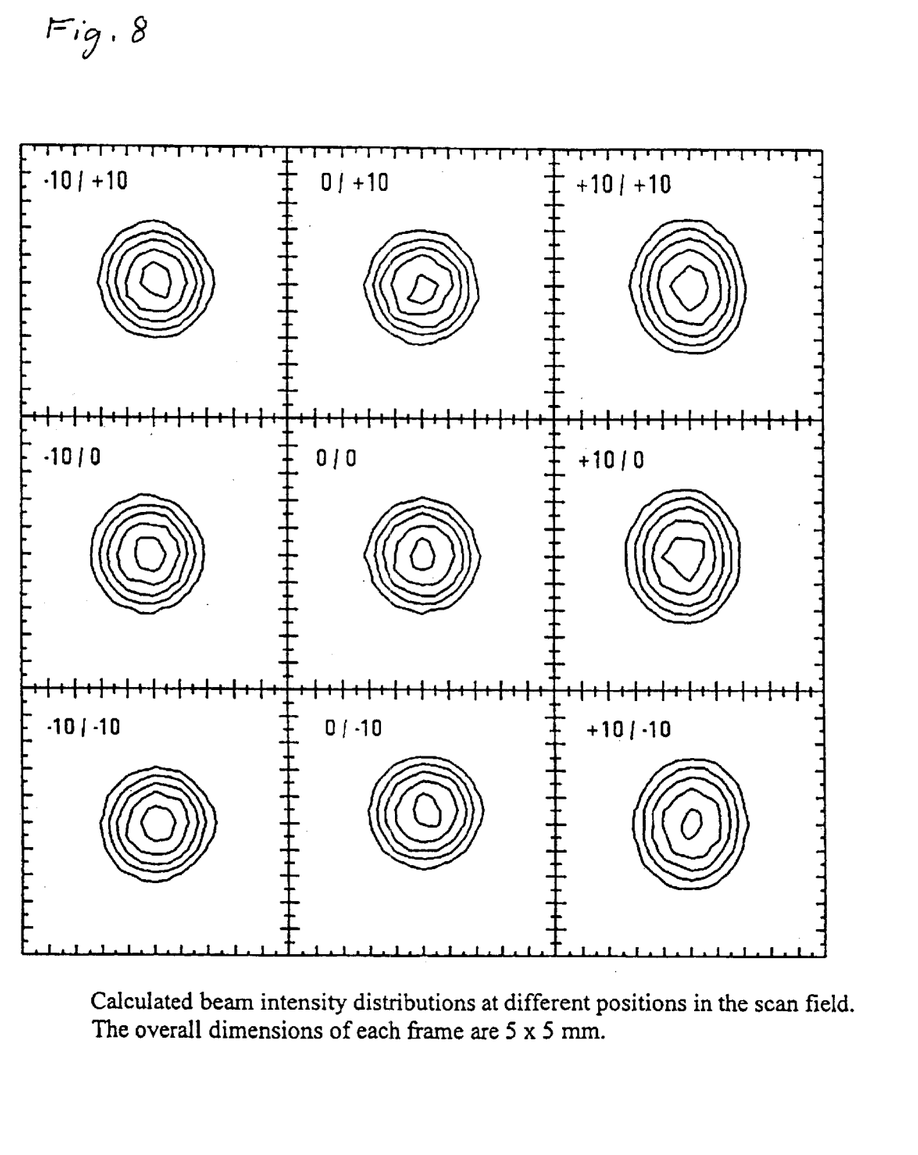
FIG. 8 shows calculated beam intensity distributions in the scan field.
Figure 9:
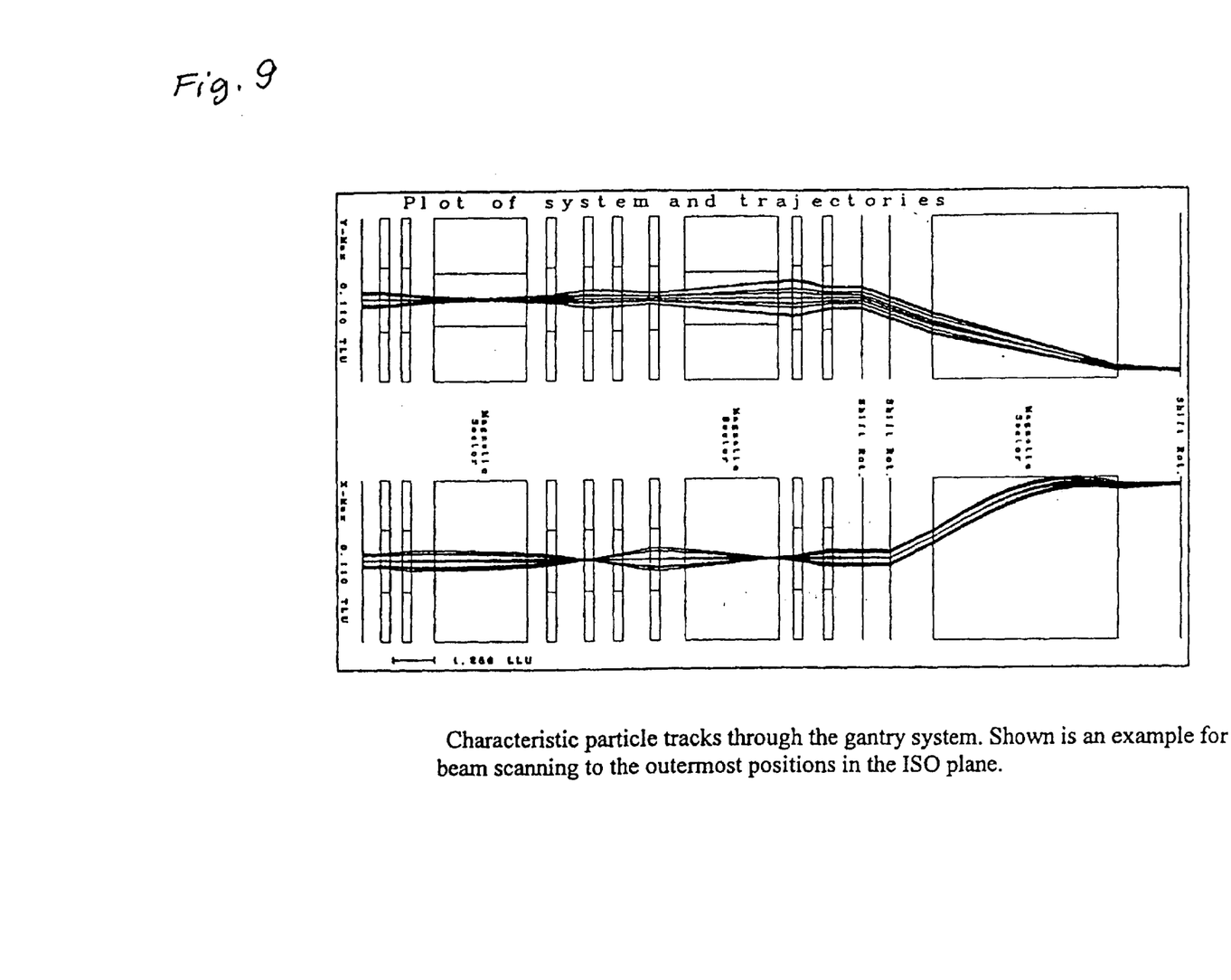
FIG. 9 shows characteristic ion beam tracks through a gantry system.

FIG. 8 shows calculated beam intensity distributions. In FIG. 8 nine frames are shown, with overall dimensions 5×5 mm of each frame FIG. 9 shows characteristic ion beam tracks through the gantry system. In FIG. 9 is shown an example for beam scanning to the outermost positions in the ISO plane.

FIG. 10 shows a scanning system 5 according to an embodiment of the present invention. FIG. 10 is self explaining in that it shows the two scanner magnets 1–2 and 3–4, one for a vertical deflection of the ion beam and another one for a horizontal deflection of the ion beam. Downstream said scanner magnets a 90 degree bending dipole 6 is positioned providing an appropriate large aperture for a scanned ion beam and a yoke element with gaps to increase the homogeneity of the electric field. Beam diagnostic plate type detectors 7 are stapled downstream of said 90 degree bending magnet 5. The entrance edge angle δ of said 90 degree bending magnet 5 has approximately the same size of 21 degree as the exit edge angle θ.

What is claimed is:

1. A scanning System for a heavy ion gantry comprising two scanner magnets (1–2; 3–4) each having:
   a maximal bending angle (α) of about 1.5 degree
   a curvature radius of about 22 m;
   a path length of about 0.6 m;
   a gap height (h) and a gap width (w) in the range of 120 mm to 150 mm;
   one glued yoke element made of up to 0.3 mm thick steel plates alloyed with up to 2% silicon having a width in the range of 300 mm to 400 mm and height in the range of 200 mm to 250 mm and a length in the range of 500 to 600 mm; and
   a coil (5) having a number of windings in the range of 50 to 70 the scanning system (11) further comprises:
   a 90 degree Dipole (6) positioned downstream of said scanner magnets (1–2; 3–4) having an aperture adapted to the scanning area, and a yoke element with gaps to increase the homogeneity of the electric field,
   beam diagnostic plate type detectors (7) stapled downstream of said 90 degree bending magnet (6).

2. The system according to claim 1, wherein said scanner magnet (1–2; 3–4) is positioned in a gantry of a heavy ion cancer therapy system upstream of the last bending magnet.

3. The system according to claim 1, wherein said coil (5) of th scanner magnet (1–2; 3–4) is designed to tolerate a maximum coil current in the range of 500 to 600 A.

4. The system according to claim 1, wherein the total coil resistance is in the range of 30 mΩ to 50 mΩ.

5. The system according to claim 1, wherein the total coil inductance is in the range of 3 mH to 4 mH.

6. The system according to claim 1, wherein the total supply voltage for said coil (5) of said scanner magnet is in the range of ±350V to ±400 V.

7. The system according to claim 1, wherein said scanner magnet (1–2; 3–4) comprises a plurality of water cooling channels and is water-cooled by a total cooling water supply in the range of 5 l/min to 10 l/min.

8. The system according to claim 1, wherein a maximum DC-power consumption of said scanner magnets (1–2; 3–4) is in the range of 10 KW to 12 KW.

9. The system according to claim 1, wherein said scanner magnet (1–2; 3–4) comprises one single yoke element.

* * * * *